US 6,706,923 B2

(12) United States Patent
Haniff et al.

(10) Patent No.: US 6,706,923 B2
(45) Date of Patent: Mar. 16, 2004

(54) PERFLUOROALKYL-SUBSTITUTED AMINES, ACIDS, AMINO ACIDS AND THIOETHER ACIDS

(75) Inventors: Marlon Haniff, West Orange, NJ (US); Ted Deisenroth, Schwörstadt (DE); John Jennings, Yonkers, NY (US); Karl Friedrich Mueller, New York City, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/202,381

(22) Filed: Jul. 24, 2002

(65) Prior Publication Data

US 2003/0153780 A1 Aug. 14, 2003

Related U.S. Application Data

(60) Provisional application No. 60/307,658, filed on Jul. 25, 2001, and provisional application No. 60/372,491, filed on Apr. 15, 2002.

(51) Int. Cl.⁷ .................. C07C 229/12; C07C 291/04; C07C 217/28; C07C 309/14; C07C 323/52
(52) U.S. Cl. .................. 564/297; 564/298; 564/485; 564/506; 562/107; 562/556; 562/567; 562/574; 252/3; 252/183.11
(58) Field of Search .................. 252/3, 183.11; 562/107, 554, 567, 574; 564/297, 298, 485, 506

(56) References Cited

U.S. PATENT DOCUMENTS

| 3,952,066 A | * | 4/1976 | Glickman et al. | .... 260/615 BF |
|---|---|---|---|---|
| 4,038,195 A | | 7/1977 | Chiesa, Jr. | ...... 252/3 |
| 4,419,298 A | | 12/1983 | Falk et al. | .......... 260/501.16 |
| 4,460,480 A | | 7/1984 | Kleiner et al. | .............. 252/8.05 |
| 4,490,304 A | * | 12/1984 | Falk | ........... 260/457 |
| 4,511,733 A | | 4/1985 | Hisamoto et al. | ........... 560/253 |
| 4,536,254 A | | 8/1985 | Falk et al. | ................ 162/135 |
| 5,091,550 A | | 2/1992 | Falk et al. | ................ 558/165 |
| 5,103,048 A | * | 4/1992 | Knaup et al. | ............... 562/568 |
| 5,218,021 A | | 6/1993 | Clark et al. | ................... 524/56 |
| 5,491,261 A | | 2/1996 | Haniff et al. | ............... 562/582 |
| 5,496,475 A | | 3/1996 | Jho et al. | ................ 252/2 |
| 5,565,193 A | | 10/1996 | Midha et al. | ........... 424/70.12 |
| 5,585,517 A | | 12/1996 | Deisenroth et al. | ......... 562/583 |
| 5,672,647 A | | 9/1997 | de La Poterie et al. | ..... 524/463 |
| 6,015,838 A | | 1/2000 | Stern et al. | ................ 516/12 |

FOREIGN PATENT DOCUMENTS

| CA | 983929 | | 2/1976 | |
|---|---|---|---|---|
| EP | 0255731 | | 2/1988 | |
| FR | 2 705 894 | * | 2/1993 | ............ A61K/7/48 |

OTHER PUBLICATIONS

McGraw–Hill Dictionary of Scientific and Technical Terms, Third Edition, p. 1577, 1984.

* cited by examiner

*Primary Examiner*—Brian Davis
(74) *Attorney, Agent, or Firm*—Kevin T. Mansfield

(57) ABSTRACT

Perfluoroalkyl-substituted amines, acids, amino acids and thioether acid compounds containing a perfluoroalkyl-iodoalkyl or perfluoroalkyl-alkene group as well as derivatives thereof, are described. They are useful as surfactants in a variety of applications where low surface tensions are required, including coating formulations for glass, wood, metal, cement, paper, textiles, as foam control agents in polyurethane foams and especially in aqueous fire-fighting formulations.

21 Claims, No Drawings

PERFLUOROALKYL-SUBSTITUTED AMINES, ACIDS, AMINO ACIDS AND THIOETHER ACIDS

This application claims the benefit under 35 U.S.C. 119(e) of U.S. Provisional Application Nos. 60/307,658, Filed Jul. 25, 2001 and 60/372,491, Filed Apr. 15, 2002.

This invention relates to perfluoroalkyl-substituted amines, acids, amino acids and thioether acids and their salts that are useful as surfactants in a wide variety of applications.

BACKGROUND OF THE INVENTION

Perfluoroalkyl ($=R_F$) substituted water soluble compounds are used primarily as specialty surfactants which can lower the surface energy of aqueous media to well below 20 dynes/cm, as compared to 25 dynes/cm for silicone based surfactants and 30 dynes/cm for conventional hydrocarbon surfactants. They are therefore useful in applications where conventional hydrocarbon and silicone-based surfactants fail, such as in coating of low free-energy surfaces such as polyolefins and oil-contaminated surfaces. $R_F$-surfactants also allow the formulation of aqueous fire-fighting systems that can be used against organic solvent fires, such as those involving burning gasoline or alcohols. Such surfactant formulations are described in U.S. Pat. Nos. 4,460,480 and 5,218,021.

While fluorosurfactants as a general rule contain only one $R_F$ group per molecule, compounds with 2 or more $R_F$ groups are useful for grease-proofing paper products used, for example in the fast food industry. Typical compounds are described in U.S. Pat. Nos. 4,419,298; 4,536,254; and 5,091,550. Typical di-$R_F$-compounds derived from amino acids, allyl glycidyl ether (AGE) and perfluoroalkyl iodides are described in U.S. Pat. No. 5,491,261.

Canadian Patent 983,929 describes mono $R_F$-substituted cationic surfactants made by reaction of an $R_F$-iodide with, first, allyl glycidyl ether (AGE), secondly, with amines and alkanolamines. No carboxylic acids or sulfonic acids are described therein.

U.S. Pat. No. 4,038,195 describes $R_F$-surfactants useful for aqueous fire fighting foams that are derived from glycine and N-methylglycine (sarcosine) by reaction with an $R_F$-oxirane prepared from allyl glycidyl ether and an $R_F$-iodide and followed by dehydrohalogenation. In this patent it is taught that the ensuing double bond improves the linearity of the molecule and its performance.

It has now been discovered that a large variety of 3-perfluoroalkyl-(2,3-ene or 2-iodo) propyl-substituted amino acids as well as thioether acids and their salts, which can be made by reaction of amines or amino acids, or of thio acids with allyl glycidyl ether, followed by reaction with a perfluoroalkyl iodide and partial or complete dehydrohalogenation and, optionally, quaternization, are excellent surfactants. They can be prepared in high yields and are useful as aqueous surfactants in a variety of applications where low surface tensions are required, including coating formulations for glass, wood, metal, cement, paper and textile materials, as active ingredients in hard surface (glass, plastic, metal, stone, laminates, etc.) cleaning products, as well as additives to dye baths, liquid laundry detergents and cosmetic products for the hair and skin, as foam control agents in polyurethane foams and especially as components in aqueous fire-fighting formulations.

The presence of the more hydrophobic 3-perfluoroalkyl-2-iodopropyl intermediate resulting from partial dehydrohalogenation may actually benefit the overall surface tension. According to Jarvis (J. Phys. Chem. 64, 150 (1960)), the solubility of a fluorochemical has a significant effect on surface activity. An increase in the organophobic part of the molecule decreases the surface tension while the solubility of the molecule also decreases. Eventually, inadequate solubility of the molecule limits the minimum surface tension that can be achieved.

BRIEF SUMMARY OF THE INVENTION

The present invention provides 3-perfluoroalkyl-(2,3-ene and/or 2-iodo) propyl-substituted amines, amino carboxylic and sulfonic acids, and thioether carboxylic, phosphoric, sulfonic and sulfuric acids, and salts and quaternized derivatives thereof, which are prepared from the corresponding amines, amino and thioether acids by reaction with allyl glycidyl ether and perfluoroalkyl iodides, followed by partial or complete dehydrohalogenation.

Another aspect of this invention relates to a substrate which contains, or has been treated with, 0.01 to 10% by weight of a fluorine-containing composition, at least part of said fluorine being provided by one of the compounds according to the present invention.

Another aspect of this invention relates to fluorine-containing aqueous fire-fighting compositions, at least part of said fluorine being provided by one of the compounds according to the present invention.

DETAILED DESCRIPTION OF THE INVENTION

The novel perfluoroalkyl amines, amino acids and thioether acids of the present invention are of the formula:

or

in which $R_1$ is an aliphatic, aromatic or cyclo-aliphatic hydrocarbon residue with one to 20 carbon atoms, optionally interrupted by one or more oxygens and/or substituted by hydroxy groups, or is $R_2$;

$R_2$ is $R_1$ or an aliphatic, aromatic or cyclo-aliphatic hydrocarbon residue with 1 to 20 carbon atoms, substituted by one or two carboxy groups or a sulfate or a sulfonate group, and which is optionally further substituted by amino or hydroxy groups and/or interrupted by tertiary amino groups, sulfur or oxygen, with the proviso that when $R_2$ is $R_1$, the compound is of structure (1b) or (1c), and when $R_2$ is —CH$_2$—COOH, $Q_F$ is $Q_{F1}$;

$R_3$ is $C_1$–$C_5$alkyl or benzyl, or is a $C_1$–$C_5$alkylene group which is substituted by a carboxy or sulfonate group;

$R_4$ is $C_1$–$C_5$alkylene or phenylene;

$A^-$ is an ionically or covalently bound anion;

M is hydrogen, an alkali metal cation, ammonium, or ammonium that is mono-, di-, tri- or tetra-substituted by $C_1$–$C_4$alkyl, $C_1$–$C_4$-hydroxyalkyl, or a mixture thereof; and $Q_F$ is 0 to 50% by weight $Q_{F1}$ and 50 to 100% by weight $Q_{F2}$, wherein $Q_{F1}$ is $R_F$CH$_2$CHI—CH$_2$—O—CH$_2$CH(OH)CH$_2$— and
$Q_{F2}$ is $R_F$CH=CH—CH$_2$—O—CH$_2$CH(OH)CH$_2$—, in which $R_F$ is a monovalent, perfluorinated, alkyl or alkenyl, linear, branched or cyclic organic radical having three to twenty fully fluorinated carbon atoms, which organic radical is optionally interrupted by divalent oxygen or sulfur atoms, with the proviso that the compound of the formula

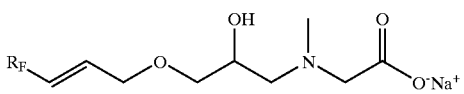

is excluded.

$A^-$ as an anion is for example an acetate, a halide such as a chloride, bromide or iodide, or is a covalently bound carboxyl or sulfonate group. $A^-$ is in particular a chloride or a covalently bound carboxyl group.

M as an alkali metal cation is, for example, a cation of sodium, lithium or potassium. M as an alkali metal cation is especially a cation of sodium.

When M is ammonium that is monosubstituted by $C_1$–$C_4$alkyl, it is, for example methyl-, ethyl-, n-propyl-, isopropyl-, n-butyl- or tert.-butylammonium.

When M is ammonium that is disubstituted by $C_1$–$C_4$alkyl, it is, for example dimethyl-, diethyl-, di-n-propyl-, diisopropyl-, or di-n-butylammonium.

When M is ammonium that is trisubstituted by $C_1$–$C_4$alkyl, it is, for example trimethyl- or triethylammonium.

When M is ammonium that is tetrasubstituted by $C_1$–$C_4$alkyl, it is preferably tetramethyl-, tetraethyl-, methyltributyl- or tetrabutylammonium.

When M is ammonium that is mono-, di-, tri- or tetra-substituted by $C_1$–$C_4$hydroxyalkyl, it is, for example diethanol-, disopropanol- or triethanolammonium, with diethanol- or triethanolammonium being particularly preferred.

M as a mixture of $C_1$–$C_4$alkyl and $C_1$–$C_4$-hydroxyalkyl is, for example methylethanolammonium.

M is in particular an ammonium or sodium cation.

The perfluoroalkyl moiety $R_F$ may be a single perfluoroalkyl group, for example perfluorohexyl, or a mixture of such groups, for example a mixture of $C_4F_9$—, $C_6F_{13}$—, $C_8F_{17}$—, $C_{10}F_{21}$—, $C_{12}F_{25}$— and $C_{14}F_{29}$— groups.

Preferred compounds according to the present invention include those wherein $Q_F$ is 80 to 100% by weight of $Q_{F2}$, and $R_F$ is saturated and contains 6 to 18 carbon atoms, is fully fluorinated and contains at least one terminal perfluoromethyl group. Most preferably, $R_F$ is a fully fluorinated, linear carbon chain with an average of about 6 to 10 carbon atoms.

Preferred compounds of formula (Ia) include those wherein $R_1$ is $C_1$–$C_4$alkyl and $R_2$ is a radical residue of a naturally occurring amino acid with two or more hydrocarbon atoms, or of p-amino-benzoic acid, aminomethane sulfonic acid, taurine or beta-alanine.

Particularly preferred compounds of formula (Ia) include those wherein $R_1$ is methyl and $R_2$ is —CH$_2$—CH$_2$—COOH or —CH$_2$CH$_2$—SO$_3$H.

Preferred compounds of formula (Ic) include those wherein $R_1$ and $R_2$ are $C_1$–$C_4$alkyl, $R_3$ is $C_1$–$C_5$alkyl or benzyl, and $A^-$ is chloride.

Additional preferred compounds of formula (Ic) include those wherein $R_1$ and $R_2$ are methyl, $R_3$ is —CH$_2$—COO$^-$, and $A^-$ forms a betaine with the quatemary nitrogen.

Preferred compounds of formula (IIa) include those wherein $R_4$ is —CH$_2$CH$_2$—, —CH(COOH)CH$_2$— or —C(COOH)=CH—.

Preferred compounds of formula (IIb) include those wherein $R_4$ is —CH$_2$CH$_2$—.

Also preferred are compounds of formula (IIIb) and (IIIc) wherein $R_1$ is $C_1$–$C_4$alkyl, especially methyl, for example the compounds $Q_F$—N(CH$_3$)—(PO$_3$)$_3$H and $Q_F$—N(CH$_3$)—SO$_3$H.

The compounds of formulae (Ia), (Ib), (Ic), (IIa) and (IIb) of this invention may be synthesized by first reacting allyl glycidyl ether with a primary or secondary amine to introduce at least one allyloxy radical, then adding an $R_F$-iodide to the resulting allyloxy radical, followed by partial or complete dehydrohalogenation.

Compounds of formulae (IIa), (IIIb) and (IIIc) of this invention may be prepared by first adding allyl glycidyl ether to a mercapto acid to introduce an allyloxy radical, followed by addition of $R_F$-iodide to the allyloxy radical, followed by partial or complete dehydrohalogenation. Interesting allyloxy compounds can be synthesized for example by addition of equimolar amounts allyl glycidyl ether (=AGE) to amines such as dimethylamine or sarcosine (N-methyl-glycine), or by addition of allyl glycidyl ether to mercaptans such as mercaptopropionic acid.

The addition of the $R_F$-iodide to the allyloxy alcohols or acids proceeds readily in the presence of a free radical initiator such as an azo compound or peroxide at conventional initiation temperatures of 35 to 150° C. It was found, however, that only in the presence of sulfite, bisulfite or dithionate ions does the reaction proceed fast enough and conversions are high enough to make the synthesis commercially practical. The novel process to make the compounds of this invention is described separately in U.S. Pat. No. 5,585,517 and in co-pending application Ser. No. 09/691,486.

A solvent can be present during the reaction. Useful solvents include for example ketones such as acetone, methyl ethyl ketone or methyl-propyl ketone, esters such as isopropyl acetate, alcohols such as ethanol or butanol, ethers such as dioxane or di-(2-hydroxyethyl)-ether, hydrocarbons such as toluene or octane, amides such as dimethylformamide and lactams such as N-methylpyrrolidone, and mixtures thereof.

Complete dehydrohalogenation is generally carried out in water at 50 to 100° C. in the presence of a strong base such as sodium or potassium hydroxide, over a period of several hours. If the product is obtained as the non-aqueous phase, it is repeatedly washed with water and finally isolated, either as a melt, by filtration or as a solution, depending on the specific product. The dehydrohalogenated product is analyzed for its hydroxyl value prior to further reaction. The trans/cis ratio is typically 85/15 according to NMR analysis. The trans isomer can be selectively obtained by employing a hindered amine base such as DABCO™ or a trialkylamine.

The compounds of the present invention are useful as surfactants in a variety of applications where a low surface tension is required, including coating formulations for glass, wood, metal, brick, concrete, cement, natural and synthetic stone, tile, synthetic flooring, paper, textile materials and plastics. In waxes and polishes for floors, furniture, shoes, automotive care and other types of hard surfaces, they improve wetting, leveling and gloss.

They are useful as active ingredients in a variety of cleaning products for hard surfaces such as glass, tile, marble, ceramic, linoleum and other plastics, metal, stone, laminates, etc. They are especially useful to achieve wetting of otherwise difficult to wet surfaces, such as oil-contaminated metals and polyolefins. Thus one aspect of this invention relates to a wetting composition, which comprises at least one compound of the present invention and a liquid carrier, and to a method of wetting a surface, which comprises contacting the surface with said wetting composition.

Their ability to wet metals makes the compounds of the present invention useful as additives for solvent cleaning and scale removal of metals and metal equipment, for metal pickling baths to increase life and acid runoff, for chrome electroplating, where they reduce surface tension and foaming and as additives for soldering flux, especially for electronic circuitry.

To wet low energy surfaces including natural and synthetic rubbers, resins and plastics, the surfactants of the present invention can be employed in synergistic mixtures with hydrocarbon surfactants.

Compounds of the present invention are also useful as wetting agents for compositions containing herbicides, fungicides, weed killers, hormone growth regulators, parasiticides, insecticides, germicides, bactericides, nematocides, microbiocides, defoliants or fertilizers, where they aid in wetting the surface the composition is applied to and, in the case of an insecticide, enhance its penetration into the insect. Likewise, in the pharmaceutical industry, the compounds of the present invention are useful to enhance penetration of therapeutic agents such as antimicrobials through the skin. They are also useful to improve the strength and homogeneity, and to reduce the permeability of encapsulated materials. They may also be used to emulsify fluorochemical blood substitutes.

The surfactants of the present invention can be incorporated into products that function as antifogging agents for glass surfaces exposed to humid atmospheres such as mirrors in bathrooms, automobile windshields and eyeglasses. These fluorosurfactants may also be incorporated into products to function as an antistatic agent for magnetic tapes, phonograph records, floppy disks, disk drives, rubber compositions, PVC, and to reduce the surface charge of polyester film.

The compounds of the present invention are also useful as foam control agents in polyurethane foams. Thus another aspect of this invention relates to a method of controlling foam during polyurethane foam manufacture, which comprises incorporating an effective foam-controlling amount of a compound according to the present invention into a polyurethane foam formulation.

They are also useful in controlling foam in other products such as spray-on oven cleaners, foamed kitchen and bathroom cleansers and disinfectants, and in aerosol shaving foams.

They are also useful in controlling foam in textile treatment baths, as a wetting agent for finish-on-yarn uniformity and as a penetrating agent for finishes on tow, heavy denier fibers.

Their ability to promote wetting and penetration makes the compounds of the present invention also useful in a variety of personal care products for hair, like shampoos, conditioners and creme rinses where they ensure even deposition of other actives as well as improve the lubricity of the hair to facilitate wet-combing. Additionally they are useful in cosmetic products for the skin such as therapeutic or protective creams and lotions, oil and water repellent cosmetic powders, deodorants and anti-perspirants, nail polish and lipstick. Compounds according to the present invention can also be used advantageously in toothpastes containing potassium fluoride to enhance fluoroapatite formation and inhibit caries. In combination with a nonionic fluoroalkylamide synergist in toothpaste, they can increase enamel-fluoride interactions.

Additionally they are useful adjuvants to household care products such as floor and furniture waxes and polishes, and to fabric care products such as stain pretreatments and/or stain removers for clothing, carpets and upholstery, as well as in laundry detergents. They are also useful as a rinse-aid for car washes and in automatic dishwashers.

Compounds according to the present invention are also useful in dry cleaning, where they improve soil suspension in perchloroethylene and reduce redeposition. They are also useful for improved wetting and leveling and as an anti-cratering adjuvant for finishes and paints.

In the plastics and rubber industry, in addition to the uses described above, compounds of the present invention also useful as emulsifying agents for polymerization, particularly of fluoromonomers, and to aid in the preparation of agglomerates of powdered fluorocarbon polymers. They are also useful as latex stabilizers, as mold release agents for silicones, etc. and as additives for elimination of trapped air in plastic laminates.

In the petroleum industry the compounds of the present invention are useful as wetting assistants for oil well treatments, drilling muds and additives to improve tertiary oil well recovery, as well as in extreme pressure EP lubricants and as a lubricating cuffing oil improver, to improve penetration times.

In the graphic arts the compounds of the present invention are also useful as wetting agents for writing inks and as printing ink additives for ink flow and leveling in both aqueous and solvent based systems. They are also useful to form ink-repellent surfaces for waterless lithographic plates and electrographic coatings. In photography the compounds of the present invention are useful as photoemulsion stabilizers, coating aids in the preparation of multiple layer film elements, as antifogging agents for films and antistatic wetting agents for film coatings as well as surfactants for developer solutions.

The compounds of the present invention are also useful as wetting agents for fighting forest fires, as a component of fluoroprotein foams, as additives to dry chemical extinguishing agents and as agents in aerosol-type extinguishers. But they are especially useful as components in aqueous fire-fighting foam formulations. Aqueous fire-fighting formulations are described for example in U.S. Pat. Nos. 4,038,195 and 5,496,475, the disclosures of which are incorporated by reference. Thus another aspect of this invention relates to fluorine-containing aqueous firefighting compositions, wherein at least part of the fluorine is provided by at least one compound according to the present invention.

Another aspect of this invention is a substrate comprising 0.01 to 10% by weight of a fluorine-containing composition, at least part of said fluorine being provided by a compound of the present invention.

The compounds of the present invention are generally applied to a substrate as a dilute aqueous phase. A typical application level is in the range of 0.01 to 0.2% by weight of a compound of the present invention based on the aqueous phase.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

Experimental Part

EXAMPLE 1

Synthesis of a Perfluoroalkyl-allyloxy Substituted Carboxy Betaine Surfactant 1A. 1-Allyloxy-3-dimethylamino-2-propanol A charge of 112.7 g (1.00 mol, 40%) dimethylamine is made to a 500 ml three-necked, round-bottomed flask. The amine is heated to 40° C. with stirring while 114.1 g (1.00 mol) allyl glycidyl ether is added over 2.5 hours while keeping the temperature below 50° C. After 3.5 hours at 50° C., GC analysis on a 30 M×0.53 mm SPB-5 polysiloxane column shows a single peak as 98% of the desired product. A viscous oil is obtained in quantitative yield. Analysis by $^1$H NMR (500 MHz, CDCl$_3$) gives the following results: δ=2.61 (6H, s, —N(C$\underline{H}_3$)$_2$), 2.62 and 2.71 (2H, m, —CH(OH)C$\underline{H}_2$N(CH$_3$)$_2$), 3.40 and 3.51 (2H, dd, —OCH$_2$CH(OH)—), 4.04 (1H, bm, —CH$_2$C$\underline{H}$(OH)CH$_2$—), 4.36 (2H, m, CH$_2$=CHC$\underline{H}_2$—), 5.13 (1H, dd, C$\underline{H}_2$=CH—, cis isomer), 5.22 (1H, dd, C$\underline{H}_2$=CH—, trans isomer), 5.80 (1H, m, CH$_2$=C$\underline{H}$—). This data supports the following structure:

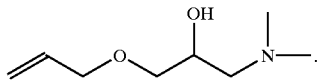

1B. 2-[3-Allyloxy-2-hydroxypropyl(dimethyl)ammonium] acetate

A mixture of 187.8 g (0.566 mol) of the product of Example 1A, 69.2 g (0.594 mol) sodium chloroacetate, and 17 g deionized water is stirred at 82° C. in a 500 ml three-necked, round-bottomed flask. A 7° C. exotherm is noted. After 4 hours, the reaction is complete as determined by silver nitrate titration for chloride. The product is dried under reduced pressure at 55° C., taken up in ethanol, then filtered and finally concentrated again to give a white crystalline product which analyzes by $^1$H NMR (500 MHz, CD$_3$OD) as follows: δ=3.35 (6H, d, —N(C$\underline{H}_3$)$_2$), 3.40 and 3.51 (2H, dd, —OC$\underline{H}_2$CH(OH)—), 3.48 (2H, m, —CH(OH)C$\underline{H}_2$N(R$_3$)$_2$), 3.93 (2H, AB quartet, —NR$_3$CH$_2$COO—), 4.04 (1H, bm, —CH$_2$C$\underline{H}$(OH)CH$_2$—), 4.36 (2H, m, CH$_2$=CHC$\underline{H}_2$—), 5.13 (1H, dd, C$\underline{H}_2$=CH—, cis isomer), 5.22 (1H, dd, C$\underline{H}_2$=CH—, trans isomer), 5.80 (1H, m, CH$_2$=C$\underline{H}$—). This data supports the following structure:

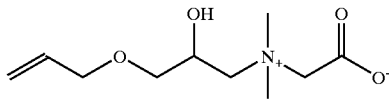

1C. R$_f$I Addition

At room temperature 68.2 g (0.153 mol) of perfluorohexyl iodide (Clariant), 71.3 g (0.153 mol) of the product of Example 1B, 1.1 g (6 mmol) 2,2'-azobis (2-methylbutyronitrile) (VAZO-67), 2.9 g (0.015 mol) sodium metabisulfite, and 13 g n-propanol are charged into a 500 ml three-necked, round-bottomed flask. The reaction mixture exotherms to 35° C. and becomes a clear, single phase. With stirring, the mixture is heated to 75–80° C. and held for 5 hours. At this time, GC analysis on a 30 M×0.53 mm SPB-5 polysiloxane column shows complete consumption of R$_f$I. The temperature is then taken to 70° C., and to the thick slurry is added portionwise 18.3 g (0.229 mol, 50%) sodium hydroxide in order to eliminate HI. After 4 hours, total elimination to the desired olefin occurs as ascertained by silver nitrate titration for iodide. The product is then diluted with water and ethanol to give a clear, yellow solution containing 30% active material in 97% yield. The product exhibits viscoelastic properties in dilute aqueous solutions. The product corresponds to the following formula:

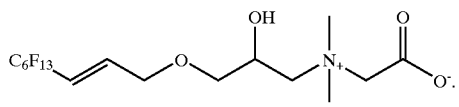

EXAMPLE 2

Using the process described in Example 1C, a mixture of R$_f$I homologs (TELA-L, DuPont) is used which has an average molecular weight MW of 506 and has the following composition in weight percent:

| $C_6F_{13}$ | $C_8F_{17}$ | $C_{10}F_{21}$ | $C_{12}F_2$ | $C_{14}F_2$ | $C_{16}F_3$ |
|---|---|---|---|---|---|
| 47.0 | 37.2 | 11.8 | 3.0% | 0.8% | 0.2% |

The product is obtained as an aqueous solution in 97.5% yield.

EXAMPLE 3

Synthesis of perfluoroalkyl-[allyloxy/iodopropyloxy] N-oxide

3A: R$_f$-iodide Addition:

Into a 500 ml three-necked, round-bottomed flask are charged at room temperature 12.7 g (0.056 mol) of the compound of Example 1A, 25.0 g (0.056 mol) perfluorohexyl iodide, 0.4 g (2.24 mmol) 2,2'-azobis (2-methylbutyronitrile) (VAZO-67), 1.1 g (5.60 mmol) sodium metabisulfite, and 4.7 g deionized water. With stirring, the mixture is heated to 75–80° C. for 3–4 hours. After this time, GC analysis on a 30 M×0.53 mm SPB-5 polysiloxane column shows complete consumption of R$_f$I. The temperature is then taken to 65° C. and to the thick slurry is added portionwise 6.7 g (0.084 mol, 50%) sodium hydroxide in order to eliminate HI. After 2 hours, total elimination to the desired olefin occurs as ascertained by silver nitrate titration for iodide. The aqueous layer is removed and the product is washed three times at 65–70° C. with 50 ml deionized water and dried under high vacuum to give an amber wax in quantitative yield. $^1$H NMR (500 MHz, CDCl$_3$) shows the following: δ=2.60 and 2.62 (6H, s,C$\underline{H}_3$N—), 2.64 and 2.78 (2H, m, —CH(OH)C$\underline{H}_2$NR$_2$), 3.51 (4H, m, —OC$\underline{H}_2$CH(OH)—), 3.92 (1H, bm, —CH$_2$CH(OH)CH$_2$—), 4.12 and 4.21 (2H, d, R$_f$CH=CHCH$_2$—), 5.63 (1H, m, R$_f$C$\underline{H}$=CH—, cis isomer), 5.94 (1H, m, R$_f$CH=CH—, trans isomer), 6.36 (1H, m, R$_f$CH=C$\underline{H}$—, cis isomer), 6.51 (1H, m, R$_f$CH=C$\underline{H}$—, trans isomer). This data supports the following structure:

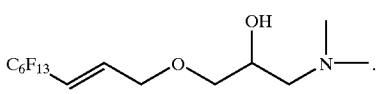

3B: Oxidation:

To 26.5 g (0.056 mol) of the product of Example 2A in 8 ml isopropanol, and 15 ml deionized water is added by dropping funnel 5.1 g (0.075 mol, 50%) hydrogen peroxide while maintaining the temperature below 60° C. After the addition, the temperature of the foamy mixture is taken to 75° C. and is held there for 4 hours to give a clear, water-soluble surfactant. $^1$H NMR analysis indicates the following structure:

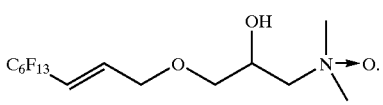

EXAMPLE 4

Synthesis of perfluoroalkyl-[allyloxy/iodopropyloxy] N-oxide Surfactant

4A: Synthesis AGE/Amine Adduct:

To a solution of 42.8 g (0.57 mol) N-methylethanolamine and 20 ml deionized water are added over 1.5 hours at 65° C. 65.0 g (0.57 mol) allyl glycidyl ether. The temperature is maintained at 70–75° C. for 4 hours, after which time the allyl glycidyl ether is completely consumed as determined by GC. The product is a dark amber solution for which $^1$H NMR data suggests the following structure:

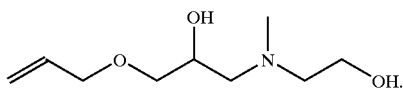

4B. $R_FI$ Addition:

Into a three-necked, round-bottomed flask, the following are charged 11.3 g (0.051 mol) of the compound of Example 3A, 22.3 g (0.050 mol) perfluorohexyl iodide, 0.4 g (2.24 mmol) 2,2'-azobis (2-methylbutyronitrile) (VAZO-67), 1.1 g (5.60 mmol) sodium metabisulfite, 7.6 g isopropanol and 4.1 g deionized water. With stirring, the mixture is heated to 75–80° C. and mixed for 3–4 hours. After this time, GC analysis on a 30 M×0.53 mm SPB-5 polysiloxane column shows complete consumption of $R_FI$. The temperature is then taken to 65° C. and to the thick slurry is added portionwise 6.4 g (0.080 mol, 50%) sodium hydroxide in order to eliminate HI. After 2 hours, total elimination to the desired olefin occurs as ascertained by silver nitrate titration for iodide. The aqueous layer is removed and the product is washed three times with 50 ml deionized water at 65° C. and dried under high vacuum to give an amber wax in quantitative yield. $^1$H NMR supports the following structure:

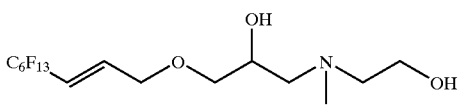

4C. Oxidation:

Following the procedure described in Example 3B, the above compound is oxidized to the corresponding N-oxide.

EXAMPLE 5

5A. 2-[3-Allyloxy-2-hydroxypropyl(methyl)amino] Acetic Acid, Sodium Salt

Into a 1 liter three-necked, round-bottomed flask is charged 121.5 g (0.438 mol, 40% in water) of sodium sarcosinate (Aldrich). The solution is heated to 60° C. with stirring and 50.0 g (0.438 mol) allyl glycidyl ether is added during 90 minutes while maintaining the temperature between 60–65° C. The reaction mixture is stirred for 2.5 hours. After this time GC analysis indicates only trace amounts of allyl glycidyl ether. The clear, yellow solution is cooled and bottled for further reactions. Spectral data: $^1$H NMR (500 MHz, CDCl$_3$): δ=2.15 and 2.60 (2H, m, —NR$_2$C$\underline{H}_2$COO—), 2.21 (3H, s, —NR$_2$C$\underline{H}_3$), 2.82 and 3.83 (2H, m, —CH(OH)C$\underline{H}_2$NR$_2$—), 3.82 (1H, bm,—CH$_2$C$\underline{H}$(OH)CH$_2$—), 4.0 (2H, d, CH$_2$=CHC$\underline{H}_2$—), 5.1 (1H, dd, C$\underline{H}_2$=CH—, cis isomer), 5.2 (1H, dd, C$\underline{H}_2$=CH—, trans isomer), 5.8 (1H, m, CH$_2$=C$\underline{H}$—). This data supports the following structure:

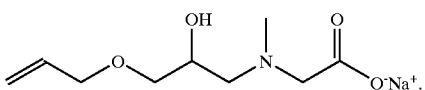

5B. $R_FI$ Addition

At room temperature 35.9 g (0.0805 mol) perfluorohexyl iodide, 35.3 g (0.0894 mol) of the compound of Example 5A, 0.7 g (3.6 mmol) 2,2'-azobis (2-methylbutyronitrile) (VAZO-67), 1.7 g (9.8 mmol) sodium metabisulfite, and 6.0 g hexylene glycol are charged into a 150 ml three-necked, round-bottomed flask. The reaction mixture exotherms to 39° C. and changes to a clear, single phase. With stirring, the mixture is heated to 75–80° C. and stirred for 5 hours. After this time, GC analysis on a 30 M×0.53 mm SPB-5 polysiloxane column shows complete consumption of $R_FI$. Titration with silver nitrate gives 40% ionic iodide. The reaction mixture is then cooled to 50° C. and diluted with 114.5 g deionized water and 10.7 g hexylene glycol to give a clear, yellow solution having 30% actives in nearly 100% yield which exhibits viscoelastic properties in dilute aqueous solutions. The product mixture contains 40% by weight of the dehalogenated olefinic compound and 60% of the iodo-compound.

5C. HI Elimination

Dehydrohalogenation is completed as in Example 4B, using sodium hydroxide to give the following compound:

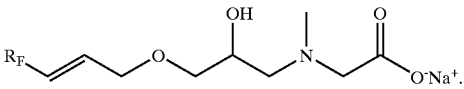

EXAMPLE 6

Using the process described in Example 5B, the mixture of $R_FI$ homologs having the $R_F$-chain length distribution and MW$_w$ shown in Example 2 is used with the allyl-oxy precursor of Example 5A to make the corresponding mixture of $R_F$-substituted sarcosinates. The mixture is obtained in 90% yield as a 25% aqueous solution.

EXAMPLE 7

Synthesis of Perfluoroalkyl-allyloxy Amphoteric Sulfonate 7A. 2-[3-Allyloxy-2-hydroxypropyl(methyl)amino]-1-ethane Sulfonic Acid, Sodium Salt Into a 1 liter three-necked, round-bottomed flask are charged 441 g (1.78 mol, 65%) sodium methyl taurate (Aldrich) and 101 g deionized water and the mixture is heated to 58–60° C. with stirring. Then 200 g (1.75 mol) allyl glycidyl ether is added over 2 hours while the temperature is maintained below 66° C. After the addition, the reaction is continued for 3 hours at 68° C. At this time, GC analysis on a 30 M×0.53 mm SPB-5 polysiloxane column shows traces of allyl glycidyl ether remaining and the formation of 5 mol percent 3-allyloxy-1,2-propanediol as a side product. The dark amber solution is cooled and bottled for further reactions. The $^1$H NMR spectral data on the product is consistent with the following structure:

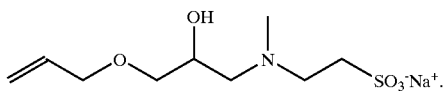

7B/C. $R_F$I Addition and Elimination of HI:

In the same manner as in Example 4B, perfluorohexyl iodide is added to the intermediate compound of Example 7A to yield a product mixture consisting of 60% dehydrohalogenated olefinic and 40% iodo product, Example 7B; this product is completely dehydrohalogenated with NaOH as in Example 4B, to give the compound of Example 7C:

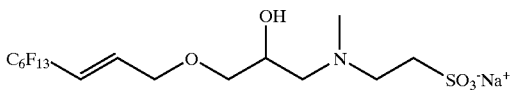

EXAMPLE 8

Using the process described in Example 5B, a mixture of $R_F$I homologs (TELA-L, DuPont) having the $R_F$-chainlength distribution and $MW_w$ shown in Example 2 is reacted with the allyloxy precursor solution of Example 7A to make the corresponding mixture of $R_F$-substituted sulfonates. The mixture is obtained in 95% yield as a 30% aqueous solution.

EXAMPLE 9

Synthesis of Perfluoro-allyloxy Thioether Carboxylate 9A. 2-thia-4-hydroxy-6-oxa-8.9-ene Nonylcarboxylic Acid, Sodium Salt A solution of 4.0 g (43.9 mmol) mercaptoacetic acid, 4.6 g (57.1 mmol, 50%) sodium hydroxide, and 2 ml deionized water is stirred at 60° C. in a round-bottomed flask. A charge of 5.0 g (43.9 mmol) allyl glycidyl ether is made to the aqueous solution over 15 minutes allowing a 20° C. exotherm. GC analysis on a 30 M×0.53 mm SPB-5 polysiloxane column shows a single product peak after 30 minutes of reaction. The clear solution (14.9 g, 95.5% yield) is cooled and bottled for further reactions. The product obtained is identified as being:

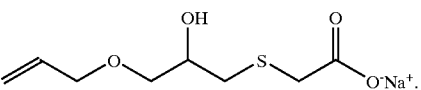

9B. $R_F$I Addition

Following the procedure in Example 1C, perfluorohexyl iodide is added to the intermediate compound of Example 6A to prepare the following product:

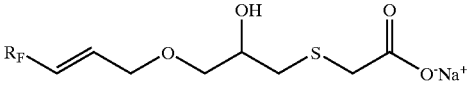

EXAMPLES 10–21

The compounds of the above examples were evaluated in distilled water and found to be particularly useful as surfactants. Table 1 shows surface tension and interfacial tension values in dynes/cm at 0.041% by weight of fluorine.

The spreading coefficient, SC, is defined in U.S. Department of Defense Military Specification MIL-F-24385D, as:

$SC=\gamma_o-\gamma_l-\gamma_{lo}$ where $\gamma_o$ is the surface tension of substrate liquid cyclohexane, $\gamma_l$ is the surface tension of spreading liquid (surfactant), and $\gamma_{lo}$ is the interfacial tension between the two liquids.

When S is >0, spontaneous spreading of the liquid, forming a thin film on the substrate liquid occurs. When S is <0, the liquid "lenses" on the substrate liquid and may fall through.

TABLE 1

| Ex. No. | $R_F$-cpd. of Ex. No. | Class of Compound | % Iodo Cpd. | Eq.S.T[2] | I.S.T.[3] | S.C.[4] |
|---|---|---|---|---|---|---|
| | | | | Dynes/cm | | |
| 10 | CONTROL[1] | $R_F$ Betaine | — | 17.2 | 7.2 | +0.9 |
| 11 | 1C | $C_6$ Betaine | 0 | 17.1 | 5.0 | +3.6 |
| 12 | 2 | $R_F$ Betaine | 0 | 18.3 | 7.6 | −0.3 |
| 13 | 3B | $C_6$ N-Oxide | 0 | 17.2 | 4.9 | +3.6 |
| 14 | 4C | $C_6$ N-Oxide | 0 | 17.0 | 4.9 | +3.8 |
| 15 | 5B | $C_6$ Amino Acid | 40 | 16.1 | 5.8 | +3.7 |
| 16 | 5C | $C_6$ Amino Acid | 0 | 17.6 | 7.7 | 0 |
| 17 | 6 | $R_F$ Amino Acid | 0 | 17.1 | 7.2 | +1.0 |
| 18 | 7B | $C_6$ Amino Sulfonate | 40 | 17.9 | 7.7 | +0.1 |
| 19 | 7C | $C_6$ Amino Sulfonate | 0 | 17.3 | 7.9 | +0.5 |
| 20 | 8 | $R_F$ Amino Sulfonate | 0 | 18.8 | 8.3 | −1.8 |
| 21 | 9B | $C_6$ Carboxylate | 0 | 21.9 | 10.0 | −6.6 |

[1]Atochem's Forafac 1157N.
[2]Equilibrium Surface Tension.
[3]Interfacial Surface Tension vs. cyclohexane.
[4]Spreading Coefficient.

These data show that several compounds exhibit very high spreading coefficient values. These compounds should give excellent film formation and sealability on a low surface tension liquid (cyclohexane). The fluorochemical betaines, N-oxides and amino acids gave high SC values, but the anionic surfactant (Example 18) did not provide a surface tension in the 16 to 18 dynes/cm range obtained in surfactants useful for AFFF fire-fighting formulations.

The Spreading Coefficient of Example 15 is considerably higher than that of the compound in Example 16 which is the fully dehydrohalogenated compound. Since the compound in Example 15 is less soluble in water, it therefore exhibits a lower interfacial tension, which is an important objective of the present invention. For comparison, Atochem's Forafac 1157N is shown as a control.

EXAMPLES 22–32

This example demonstrates the sealing power of selected fluorosurfactants on cyclohexane in a typical AFFF fire-fighting formulation. A 3% premix of the test concentrate is made in both synthetic seawater and soft water and visual seal is recorded in seconds according the procedure outlined in MIL-Spec MIL-F-24385D. The percentage value indicates percent coverage after 60 seconds.
Test results are summarized in Table 2.

TABLE 2

| Ex. No. | $R_F$-Cpd. of Ex. No | Class of Compound | Visual Seal in Synthetic Sea Water, Seconds | Visual Seal in Soft Water, Seconds |
|---|---|---|---|---|
| 22 | Forafac 1157N | $R_F$ Betaine | 30 | 34 |
| 23 | 1C | $C_6$ Betaine | 5 | 10 |
| 24 | 2 | $R_F$ Betaine | 40 | 45 |
| 25 | 3B | $C_6$ N-Oxide | 8 | 4 |
| 26 | 4C | $C_6$ N-Oxide | 6 | 5 |
| 27 | 5B | $C_6$ Amino Acid | 6 | 4 |
| 28 | 5C | $C_6$ Amino Acid | 7 | 7 |
| 29 | 6 | $R_F$ Amino Acid | 50 | 45 |
| 30 | 7B | $C_6$ Amino Sulfonate | 4 | 4 |
| 31 | 7C | $C_6$ Amino Sulfonate | 5 | 6 |
| 32 | 8 | $R_F$ Amino Sulfonate | 50 | 26 |

Regardless of the hydrophilic head group, compounds with $C_6$—$R_F$ tails were considerably faster in sealing than those having $R_F$ tails with a mixture of higher homologs.

EXAMPLE 33

33A: Reaction of cis-1,2,3,6-tetrahydrophthalic Anhydride (THPA) with 3-Dimethylamino-propylamine:

A three neck round bottom flask is charged with 40.0 g (0.2628 moles) THPA. The contents are heated to 120° C. and 26.8 g (0.262 moles) of 3-dimethylaminopropylamine are slowly added over 20 minutes with stirring. The reaction mixture is then stirred for 3 hours at 120° C. The clear orange liquid solidified to a beige-colored product upon cooling to 50° C.

33B: Addition of $R_FI$:

11.2 g (0.04318 moles) of the reaction product of Example 33A are charged into a 300 ml three neck flask fitted with a mechanical stirrer, condenser and nitrogen sparge inlet; then 5.0 g of water and 5.2 g of 50% NaOH are added and the contents of the flask are stirred for 30 minutes, followed by addition of 5.0 g of t-butanol and 21.42 g (0.0423 moles) of $R_FI$ (DuPont's Zonyl TELA-L). The mixture is stirred at 72° C. To the reaction mixture a solution of 0.33 g (2.16 mmoles) Rongalite (trade name for the addition product of formaldehyde and sodium dithionite) in 0.7 g water is added. The progress of the reaction is followed by gas chromatography. The contents are stirred at 75° C. for 4 hours. Then 4.4 g of 50% NaOH solution are added and the mixture is stirred at 75° C. After 6 hours iodide titration shows that dehydrohalogenation is complete. The mixture is neutralized with dilute HCl and t-butanol and reaction salts are removed by splitting at ambient temperature. Then 82.5 g of water and 1.2 g of ammonium hydroxide is added to the mixture to yield a clear amber mixture. The resulting amber dispersion has a pH of 9 and a fluorine content of 4.1%.

EXAMPLE 34

34A: Synthesis of 1-methylpiperazine—allyl Glycidyl Ether (AGE) Adduct:

46.09 g (46.0 mmol) of 1-methylpiperazine and 12.0 g of deionized water are placed into a round-bottomed flask equipped with a stirrer, nitrogen inlet and a thermoregulator. This mixture is heated with stirring. When a temperature of 55° C. is reached, 50.0 g (43.8 mmol) allyl glycidyl ether (AGE) is added over a one-hour period. The reaction mixture is then stirred for two hours at 60° C., after which time the reaction is complete as determined by gas chromatography. This product is obtained as a clear yellow solution of 88.0% solids by weight.

34B: Addition of $R_F$-iodide:

50.0 g (20.2 mmol AGE) of the product from Example 34A are placed into a round-bottomed flask equipped with a stirrer, nitrogen inlet and a thermoregulator and heated. The temperature is then lowered to 30° C., and 100.2 g (19.8 mmol) of perfluoroalkyl iodide (ZONYL TELA-L) and 2.4 g (1.2 mmol) of sodium dithionite are added along with 13.5 g 2-propanol. Stirring is continued for five hours at 40° C. After five hours conversion of $R_F$-iodide, as determined by gas chromatography, is >95%. A charge of 36.3% sodium hydroxide (18.6 g, 23.2, is added to the mixture, which is then stirred at 60–62° C. for 5 hours to carry out the dehydrohalogenation (reaction monitored by GC and AgNO$_3$ titration for iodide). Then 16.65 g (16.9 mmol) concentrated hydrochloric acid (37%) is added along with 400 g of deionized water to formulate the reaction mixture. The product is a semi-viscous brown/black mixture of 24.4% solids by weight and containing 8.8% F.

EXAMPLE 35

Synthesis of Perfluoroalkyl-allyloxy Anionic Surfactant

35A. Reaction of 3-allyloxy-2-hydroxy Sulfonic Acid, Sodium Salt with Perfluoroalkyl Iodide Into a 1 liter three-necked, round-bottomed flask are charged 250 g (0.458 mol, 40% by weight) of 3-alloxy-2-hydroxy-1-propanesulfonic acid, sodium salt (Aldrich) along with 40.0 g of hexylene glycol and the mixture is heated to 78–80° C. with stirring. Then 213.39 g (0.4216 mol) Zonyl TelA-L and 3.5 g (0.0229 mol) Rongalite is added over 1–2 hours while the temperature is maintained below 80° C. After the addition, stirring is continued for 3 hours at about 78° C. At this time, GC analysis on a 30 M×0.53 mm SPB-5 polysiloxane column shows none of the Zonyl TelA-L remaining. The temperature is then lowered to 65–70° C., and to the thick slurry is added portionwise 52.0 g (0.65 mol, 50%) sodium hydroxide in order to eliminate HI. After 4 hours, total elimination to the desired olefin occurs as ascertained by silver nitrate titration for iodide. The product is then diluted with water and hexylene glycol to give a clear, yellow solution containing 21.1% active material in 99% yield. The product corresponds to the following formula:

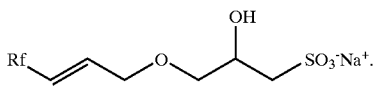

35B/C. $R_FI$ Addition and Elimination of HI:

In the same manner as in Example 35A, perfluorohexyl iodide is added to the 3-alloxy-2-hydroxy-1-propanesulfonic acid, sodium salt (Aldrich). This product is completely dehydrohalogenated with NaOH as in Example 35A, to give the compound of Example 35C:

The ability of various products of the above examples to lower surface tension and control foam was evaluated versus state of the art compounds according to standard test procedures. The following results were obtained.

| Example | Equilibrium Surface Tension[1] (dynes/cm) | Interfacial Surface Tension[2] (dynes/cm) | Foam Height[3] 0.1% (mm) |
|---|---|---|---|
| Betaine type | | | |
| Forafac 1157[4] | 16.7 | 6.2 | 210/175 |
| Example 2 | 18.7 | 8.5 | 39/36 |
| Amphoteric type | | | |
| Lodyne S-100[5] | 21.0 | 8.7 | 163/151 |
| Example 33B | 20.1 | 5.5 | 15.6/13.3 |
| Example 6 | 17.4 | 7.7 | 219/183 |
| Anionic type | | | |
| Lodyne S-103[5] | 19.9 | 7.4 | 234/209 |
| Example 35C | 17.3 | 17.8 | ND |
| Example 35A | 16.1 | 13.3 | 209/176 |
| Cationic type | | | |
| Lodyne S-106A[5] | 28.6 | 18.8 | 114/109 |
| Example 34B | 22.7 | ND | ND |

[1] Wilhemy Plate Technique, Kruss K-10 Tensiometer at 0.1% actives.
[2] ASTM Method D-1331-56 at 0.1% actives.
[3] ASTM Method D-1173-53 at 49° C.; foam height in mm, initially and after 5 minutes.
[4] A fluorosurfactant commercially available from Ciba Specialty Chemicals Corporation, High Point, North Carolinia.

The following non-limiting formulation examples illustrate various ways in which the compounds according to the invention can be used. In the formulations, all ingredient concentrations are on an active basis weight unless otherwise indicated.

EXAMPLE 36
Glass & Surface Cleaner with Anti-fog Properties

| Ingredient | Wt. % |
|---|---|
| Isopropanol | 4.00 |
| Ethylene glycol n-butyl ether | 2.50 |
| Sodium lauryl sulfate | 0.10 |
| Compound 35C | 0.20 |
| Ammonium hydroxide | 0.60 |
| Deionized water | q.s. 100% |

Compound 35C is replaced by Compound 1C, 2, 5B or C, 6, 7B or C, 8, 9B, 33 or Compound 35A to prepare analogous formulations.

EXAMPLE 37
Antistatic Plastic Cleaner

| Ingredient | Wt. % |
|---|---|
| Polydimethylsiloxane (55% active) | 2.00 |
| Sodium lauryl sulfate | 1.00 |
| Compound 35A | 0.03 |
| Distilled water | q.s. 100% |

Compound 35A is replaced by Compound 1C, 2, 5B or C, 6, 7B or C, 8, 9B, 33 or Compound 35C to prepare analogous formulations.

EXAMPLE 38
Floor Cleaner with Degreaser

| Ingredient | Wt. % |
|---|---|
| Isopropanol | 4.00 |
| Ethylene glycol n-butyl ether | 2.50 |
| Sodium dodecyl benzene sulfonate | 0.20 |
| Sodium lauryl sulfate | 0.10 |
| Compound 9B | 0.03 |
| Sodium polyacrylate | 0.10 |
| Ammonium hydroxide | 0.16 |
| Deionized water | q.s. 100% |

Compound 9B is replaced by Compound 1C, 2, 5B or C, 6, 7B or C, 8, 33 or Compound 35A or C to prepare analogous formulations.

EXAMPLE 39
Disinfecting Kitchen & Bathroom Cleaner

| Ingredient | Wt. % |
|---|---|
| Alkyl dimethylbenzylammonium chloride (80% actives) | 0.06 |
| Compound 34 | 0.01 |
| Deionized water | q.s. 100% |

Compound 34 is replaced by Compound 1C, 5B or C, 6, 7B or C, 8, 33 or Compound 33 to prepare analogous formulations.

EXAMPLE 40
Metal De-Oiling Liquid Concentrate

| Ingredient | Wt. % |
|---|---|
| Sodium silicate (37.5% active) | 12.00 |
| Tetrasodium EDTA (37% active) | 16.00 |
| Sodium xylene sulfonate (40% active) | 20.00 |
| $C_9$–$C_{11}$ linear alcohol ethoxylate, 6 Moles EO | 3.00 |
| $C_9$–$C_{11}$ linear alcohol ethoxylate, 2.5 Moles EO | 7.00 |
| Compound 3B | 0.02 |
| Water | q.s. 100% |

Compound 3B is replaced by Compound 4C to prepare an analogous formulation.

EXAMPLE 41
Concrete Stain Remover

| Ingredient | Wt. % |
|---|---|
| Sodium tripolyphosphate | 1.25 |
| Sodium metasilicate pentahydrate | 0.62 |
| Sodium sulfate | 0.40 |
| Epsom salt | 0.10 |
| Octylphenoxypolyethoxyethanol, 9–10 moles EO | 0.10 |
| Compound 33 | 0.02 |
| Sodium perborate monohydrate | 1.90 |
| Deionized water | q.s. 100% |

Compound 33 is replaced by Compound 1C, 2, 5B or C, 6, 7B or C, 8, 35A or C to prepare analogous formulations.

EXAMPLE 42
Manual Toilet Bowl Cleaner

| Ingredient | Wt. % |
| --- | --- |
| Compound 4C | 0.10 |
| Coconut diethanolamide | 2.50 |
| thickener (50% active) | 1.00 |
| Fragrance | 0.40 |
| Blue dye | 0.002 |
| Preservative | 0.10 |
| Deionized water | q.s. 100% |

Compound 4C is replaced by Compound 3B to prepare an analogous formulation.

EXAMPLE 43
Drain Cleaner

| Ingredient | Wt. % |
| --- | --- |
| Sodium hypochlorite | 10.00 |
| Sodium hydroxide | 2.00 |
| Sodium metasilicate pentahydrate | 1.00 |
| Sodium dodecyl diphenyl disulfonate | 0.10 |
| Sodium lauroyl sarcosinate | 0.90 |
| Amine oxide | 0.75 |
| Compound 7C | 0.02 |
| Water | q.s. 100% |

Compound 7C is replaced by Compound 1C, 2, 5B or C, 6, 7B, 8, 9B, 35A or C to prepare analogous formulations.

EXAMPLE 44
Drain Cleaner

| Ingredient | Wt. % |
| --- | --- |
| N-methyl-2-pyrrolidone | 10.00 |
| Compound 3B | 0.13 |
| Sodium thioglycolate | 3.60 |
| thickener (30% active) | 1.50 |
| Sodium hydroxide (10% active) | 0.80 |
| Water | q.s. 100% |

Compound 3B is replaced by Compound 4C to prepare an analogous formulation.

EXAMPLE 45
Carpet Cleaner

| Ingredient | Wt. % |
| --- | --- |
| Sodium lauryl sulfate | 0.90 |
| Ethylene glycol hexyl ether | 0.75 |
| Isopropanol | 2.00 |
| Compound 35C | 0.10 |
| Tetrasodium EDTA | 0.38 |
| Fragrance | 0.20 |
| Preservative | 0.05 |
| Citric acid | 0.11 |
| Deionized water | q.s. 100% |

Compound 35C is replaced by Compound 1C, 2, 5B or C, 6, 7B or C, 8, 9B, 33 or Compound 35A to prepare analogous formulations.

EXAMPLE 46
Carpet and Upholstery Cleaner with Oil Repellency

| Ingredient | Wt. % |
| --- | --- |
| Compound 35C | 0.20 |
| Sodium lauryl sulfate (30% active) | 5.00 |
| Ethylene glycol hexyl ether | 1.00 |
| Tetrasodium EDTA (38% active) | 0.25 |
| Sodium citrate, anhydrous | 0.50 |
| Deionized water | q.s. 100% |

Compound 35C is replaced by Compound 1C, 2, 5B or C, 6, 7B or C, 8, 9B, 33 or Compound 35A to prepare analogous formulations.

EXAMPLE 47
Laundry Spot Pretreatment

| Ingredient | Wt. % |
| --- | --- |
| $C_9$–$C_{11}$ linear alcohol ethoxylate, 8 Moles EO | 4.17 |
| $C_{12}$–$C_{15}$ linear alcohol ethoxylate, 3 moles EO | 0.83 |
| Lauric diethanolamide | 5.00 |
| Diethylene glycol methyl ether | 5.00 |
| Diethylene glycol hexyl ether | 5.00 |
| Compound 4C | 0.16 |
| Deionized water | q.s. 100% |

Compound 4C is replaced by Compound 3B to prepare an analogous formulation.

EXAMPLE 48
Home Dry Cleaning Composition

| Ingredient | Wt. % |
| --- | --- |
| $C_9$–$C_{11}$ linear alcohol ethoxylate, 8 moles EO | 0.10 |
| $C_{12}$–$C_{15}$ linear alcohol ethoxylate, 3 moles EO | 0.02 |
| Compound 3B | 0.06 |
| Ethanol | 2.00 |
| Deionized water | q.s. 100% |

Compound 3B is replaced by Compound 4C to prepare an analogous formulation.

EXAMPLE 49
Liquid Car Polish

| Ingredient | Wt. % |
| --- | --- |
| Mineral Spirits | 27.00 |
| Acrylic acid thickener | 1.00 |
| Dimethylsiloxane | 2.00 |
| Oleic acid | 1.50 |
| Morpholine | 1.30 |
| Compound 3B | 0.05 |
| Abrasive | 9.00 |
| Deionized water | q.s. 100% |

Compound 3B is replaced by Compound 4C to prepare an analogous formulation.

EXAMPLE 50
Windshield Washer Fluid with De-Icer

| Ingredient | Wt. % |
| --- | --- |
| Methanol | 30.00 |
| Sodium lauryl sarcosinate | 0.02 |
| Compound 5C | 0.02 |
| Deionized water | q.s. 100% |

Compound 5C is replaced by Compound 1C, 2, 5B, 6, 7B or C, 8, 9B, 33 or Compound 35A or B to prepare analogous formulations.

EXAMPLE 51
Shoe Cream

| Ingredient | Wt. % |
| --- | --- |
| Montan wax | 10.90 |
| Paraffin wax, soft | 14.50 |
| Rosin | 3.60 |
| Potassium carbonate | 2.20 |
| Compound 33 | 0.05 |
| Water | q.s. 100% |

Compound 33 is replaced by Compound 1C, 2, 5B or C, 6, 7B or C, 8, 35A or C to prepare analogous formulations.

EXAMPLE 52
Liquid Furniture Polish

| Ingredient | Wt. % |
| --- | --- |
| Carnauba Wax | 3.20 |
| Beeswax | 1.30 |
| Ceresin wax | 1.30 |
| Naphtha | 26.00 |
| Stearic acid | 2.60 |
| Triethanolamine | 1.50 |
| Compound 3B | 0.04 |
| Water | q.s. 100% |

Compound 3B is replaced by Compound 4C to prepare an analogous formulation.

EXAMPLE 53
Floor Polish

| Ingredient | Wt. % |
| --- | --- |
| Diethylene glycol monomethyl ether | 45.85 |
| Compound 35A | 0.015 |
| Tributoxy ethylphosphate | 1.50 |
| Preservative | 0.02 |
| Latex emulsion (38% active) | 38.10 |
| High density oxidized PE homopolymer (40% emulsion) | 5.00 |
| Ethylene-acrylic acid copolymer (25% emulsion) | 5.00 |
| Water | q.s. 100% |

Compound 35A is replaced by Compound 1C, 2, 5B or C, 6, 7B or C, 8, 33 or 35C to prepare analogous formulations.

EXAMPLE 54
Spray and Wipe Multi-Purpose Cleaner

| Ingredient | Wt. % |
| --- | --- |
| Octylphenoxy polyethoxyethanol, 9–10 moles EO | 0.25 |
| Compound 4C | 0.02 |
| Diethylene glycol methyl ether | 2.50 |
| Isopropanol | 2.50 |
| Deionized water | q.s. 100% |

Compound 4C is replaced by Compound 3B to prepare an analogous formulation.

EXAMPLE 55
Corrosion Resisting Coating

| Ingredient | Wt. % |
| --- | --- |
| Castor Oil | 40.00 |
| Undecylenic acid | 10.00 |
| Compound 35A | 0.04 |
| Copper oxide | 1.00 |
| Iron oxide | 1.00 |
| Mineral spirits | 24.00 |
| Denatured ethanol | q.s. 100% |

Compound 35A is replaced by Compound 1C, 2, 5B or C, 6, 7B or C, 8, 33 or 35C to prepare analogous formulations.

EXAMPLE 56
Car Wash

| Ingredient | Wt. % |
| --- | --- |
| Dodecyl benzene sulfonic acid | 16.30 |
| Sodium hydroxide (50% active) | 4.35 |
| Coconut diethanolamine | 2.05 |
| Sodium xylene sulfonate (40% active) | 12.50 |
| Ammonium lauryl ether sulfate, 3 Moles EO | 3.00 |
| Nonyl phenoxy-polyethoxyethanol | 2.00 |
| Compound 35C | 0.10 |
| Water | q.s. 100% |

Compound 35C is replaced by Compound 1C, 2, 5B or C, 7B or C, 8, 33 or 35A to prepare analogous formulations.

EXAMPLE 57
Pump Hair Spray

| Ingredient | Wt. % |
| --- | --- |
| Ethanol, 200 proof | 84.50 |
| 60% t-butyl acrylate/20% acrylic acid/20% silicone copolymer | 3.00 |
| KOH (45%) | 0.90 |
| Isododecane | 5.00 |
| Compound 1C | 0.05 |
| Water | q.s. 100% |

Compound 1C is replaced by Compound 2, 5B or C, 6, 7B or C, 8, 33, 35A or C to prepare analogous formulations.

EXAMPLE 58
Colored Nail Varnish

| Ingredient | Wt. % |
| --- | --- |
| Polyurethane dispersion (40% in water) | 50.00 |
| Pigments | 1.50 |
| Thickener of the polyurethane type | 3.00 |
| Compound 7C | 0.05 |
| Water | q.s. 100% |

Compound 7C is replaced by Compound 1C, 2, 5B or C, 6, 7B, 8, 33, 35A or 35C to prepare analogous formulations.

What is claimed is:

1. A compound of the formula:

$Q_F$—$NR_1R_2$ (Ia), $Q_F$—$N(\rightarrow O)R_1R_2$ (Ib), $Q_F$—$N^+R_1R_2R_3A^-$ (Ic), $Q_F$—S—$R_4$—COOM (IIa), $Q_F$—$S(O)_2$—$R_4$—COOM (IIb), $Q_F$—$SO_3M$ (IIIa), $Q_F$—$NR_1$—$(PO_3)_3M$ (IIIb)

or $Q_F$—$NR_1$—$SO_3M$ (IIIc), in which $R_1$ is an aliphatic, aromatic or cyclo-aliphatic hydrocarbon residue with one to 20 carbon atoms, optionally interrupted by one or more oxygens and/or substituted by hydroxy groups, or is $R_2$;

$R_2$ is $R_1$ or an aliphatic, aromatic or cyclo-ahiphatic hydrocarbon residue with 1 to 20 carbon atoms, substituted by one or two carboxy groups or a sulfate or a sulfonate group, and which is optionally further substituted by amino or hydroxy groups and/or interrupted by tertiary amino groups, sulfur or oxygen, with the proviso that when $R_2$ is $R_1$, the compound is of structure (1b) or (1c), and when $R_2$ is —$CH_2$—COOH, $Q_F$ is $Q_{F1}$;

$R_3$ is $C_1$–$C_5$alkyl or benzyl or is a $C_1$–$C_5$alkylene group which is substituted by a carboxy or sulfonate group;

$R_4$ is $C_1$–$C_5$alkylene or phenylene;

$A^-$ is an ionically or covalently bound anion;

M is hydrogen, an alkali metal cation, ammonium, or ammonium that is mono-, di-, tri- or tetra-substituted by $C_1$–$C_4$alkyl, $C_1$–$C_4$-hydroxyalkyl, or a mixture thereof; and $Q_F$ is 0 to 50% by weight $Q_{F1}$ and 50 to 100% by weight $Q_{F2}$, wherein $Q_{F1}$ is $R_FCH_2CHI$—$CH_2$—O—$CH_2CH(OH)CH_2$— and $Q_{F2}$ is $R_FCH$=CH—$CH_2$—O—$CH_2CH(OH)CH_2$—, in which $R_F$ is a monovalent, perfluorinated, alkyl or alkenyl, linear, branched or cyclic organic radical having three to twenty fully fluorinated carbon atoms, which organic radical is optionally interrupted by divalent oxygen or sulfur atoms, with the proviso that the compound of the formula

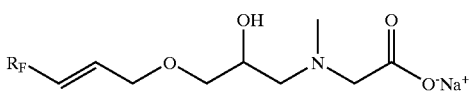

is excluded.

2. A compound according to claim 1, wherein $A^-$ is an acetate, a chloride, bromide, or iodide, or is a covalently bound carboxyl or sulfonate group.

3. A compound according to claim 1, wherein M is a cation of sodium, lithium or potassium.

4. A compound according to claim 1, wherein $R_F$ is a single perfluoroalkyl group or a mixture of such groups.

5. A compound according to claim 4, wherein $R_F$ is perfluorohexyl or a mixture of $C_4F_9$—, $C_6F_{13}$—, $C_8F_{17}$—, $C_{10}F_{21}$—, $C_{12}F_{25}$— and $C_{14}F_{29}$— groups.

6. A compound of formula (Ia), (Ib), (Ic), (IIa) or (IIb) according to claim 1, wherein $Q_F$ is 80 to 100% by weight of $Q_{F2}$, and $R_F$ is saturated and contains 6 to 18 carbon atoms, is fully fluorinated and contains at least one terminal perfluoromethyl group.

7. A compound according to claim 6, wherein $R_F$ is a fully fluorinated, linear carbon chain with an average of about 6 to 10 carbon atoms.

8. A compound of formula (Ia) according to claim 1, wherein $R_1$ is $C_1$–$C_4$alkyl and $R_2$ is a radical residue of a naturally occurring amino acid with two or more hydrocarbon atoms, or of p-aminobenzoic acid, aminomethane sulfonic acid, taurine or beta-alanine.

9. A compound of formula (Ia) according to claim 8, wherein $R_1$ is methyl and $R_2$ is —$CH_2$—$CH_2$—COOH or —$CH_2CH_2$—$SO_3H$.

10. A compound of formula (Ic) according to claim 1, wherein $R_1$ and $R_2$ are $C_1$–$C_4$alkyl, $R_3$ is $C_1$–$C_5$alkyl or benzyl, and $A^-$ is chloride.

11. A compound of formula (Ic) according to claim 1, wherein $R_1$ and $R_2$ are methyl, $R_3$ is —$CH_2$—$COO^-$, and $A^-$ forms a betaine with the quaternary nitrogen.

12. A compound of formula (IIa) according to claim 1, wherein $R_4$ is —$CH_2CH_2$—, —CH(COOH)$CH_2$— or —C(COOH)=CH—.

13. A compound of formula (IIb) according to claim 1, wherein $R_4$ is —$CH_2CH_2$—.

14. A process for the preparation of a compound of formula (Ia), (Ib), (Ic), (IIa) or (IIb) according to claim 1, which comprises first reacting allyl glycidyl ether with a primary or secondary amine to introduce at least one allyloxy radical, then adding an $R_F$-iodide to the resulting allyloxy radical, followed by partial or complete dehydrohalogenation.

15. A process for the preparation of a compound of formula (IIIa), (IIIb) or (IIIc) according to claim 1, which comprises first reacting allyl glycidyl ether with a mercapto acid to introduce an allyloxy radical, then adding an $R_F$-iodide to the resulting allyloxy radical, followed by partial or complete dehydrohalogenation.

16. A composition, which comprises at least one compound according to claim 1 and a liquid carrier.

17. A composition according to claim 16, which comprises 0.01 to 0.2% by weight of the compound in an aqueous carrier.

18. A method of wetting a surface, which comprises contacting the surface with a composition according to claim 16.

19. A method of controlling foam during polyurethane foam manufacture, which comprises incorporating an effective foam-controlling amount of a compound according to claim 1 into a polyurethane foam formulation.

20. A fluorine-containing aqueous firefighting composition, wherein a compound according to claim 1 provides all or at least a part of the fluorine.

21. A surface comprising 0.01 to 10% by weight of a fluorine-containing composition, all or at least a part of said fluorine being provided by a compound according to claim 1.

* * * * *